(12) United States Patent
Hehemann et al.

(10) Patent No.: US 8,759,039 B2
(45) Date of Patent: Jun. 24, 2014

(54) PORPHYRANASES, AND USE THEREOF FOR HYDROLYZING POLYSACCHARIDES

(75) Inventors: Jan-Hendrik Hehemann, Roscoff (FR); Gaëlle Correc, Santec (FR); Gurvan Michel, Roscoff (FR); Tristan Barbeyron, Cleder (FR); William Helbert, Roscoff (FR); Mirjam Czjzek, Plougoulm (FR)

(73) Assignee: Centre National de la Recherche Scientifique (C.N.R.S.), Paris (FR)

( * ) Notice: Subject to any disclaimer, the term of this patent is extended or adjusted under 35 U.S.C. 154(b) by 48 days.

(21) Appl. No.: 13/386,361

(22) PCT Filed: Jul. 20, 2010

(86) PCT No.: PCT/FR2010/051530
§ 371 (c)(1),
(2), (4) Date: Apr. 6, 2012

(87) PCT Pub. No.: WO2011/010062
PCT Pub. Date: Jan. 27, 2011

(65) Prior Publication Data
US 2012/0190836 A1 Jul. 26, 2012

(30) Foreign Application Priority Data
Jul. 21, 2009 (FR) .................................. 09 55070

(51) Int. Cl.
| C12P 19/14 | (2006.01) |
| C12P 19/12 | (2006.01) |
| C12P 19/04 | (2006.01) |
| C12N 9/26 | (2006.01) |
| C12N 15/00 | (2006.01) |
| C12N 5/00 | (2006.01) |
| C12N 5/04 | (2006.01) |
| C12N 1/20 | (2006.01) |
| C12N 1/00 | (2006.01) |
| C12N 1/12 | (2006.01) |

(52) U.S. Cl.
USPC ............. 435/99; 435/100; 435/101; 435/201; 435/320.1; 435/325; 435/419; 435/252.3; 435/254.11; 435/257.2

(58) Field of Classification Search
None
See application file for complete search history.

(56) References Cited

FOREIGN PATENT DOCUMENTS

JP 2007236236 A * 9/2007

OTHER PUBLICATIONS

Ohta et al., "Purification and Characterization of a Novel a-Agarase from a Thalassomonas sp.", Curr. Microbiol. 50:212-216, 2005.*
Sonnenburg, J., "Genetic pot luck", Nature 464:837-838, Apr. 2010.*
Database UniProt [Online], "SubName: Full=MS132, putative beta-agarase," EBI accession No. UNIPROT: Q93P99 (2001).
Hehemann et al., "Transfer of carbohydrate-active enzymes from marine bacteria to Japanese gut microblota," *Nature*, 464(7290): 908-912 (2010).
Hatada et al., "Hyperproduction and application of alpha-agarase to enzymatic enhancement of antioxidant activity of porphyran," *J. Agricultural Food Chem.*, 54(26): 9895-9900 (2006).
Zhao et al., "Degradation of porphyran from Porphyra haitanensis and the antioxidant activities of the degraded porphyrans with different molecular weight," *Int'l. J. Bio. Macromolecules*, 38(1): 45-50 (2006).
Zhong et al., "Sequence analysis of a 101-kilobase plasmid required for agar degradation by a Microscilla isolate," *Appl. Environ. Microbiol.*, 67(12): 5771-5779 (2001).
Int'l Search Report and Written Opinion issued in app. No. PCT/FR2010/051530 (2010).

* cited by examiner

*Primary Examiner* — David J Steadman
(74) *Attorney, Agent, or Firm* — Barnes & Thornburg LLP

(57) ABSTRACT

The present invention relates to the isolation and to the characterization of two proteins having a novel enzymatic activity, i.e. a porphyranase activity. These proteins are useful for hydrolyzing polysaccharides containing sulfated agaro-colloids and for producing oligo-porphyrans, notably oligo-porphyrans with a defined structure and size.

8 Claims, 6 Drawing Sheets

A)
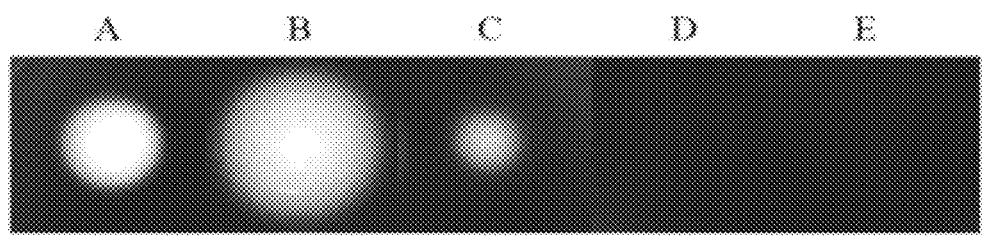
B)
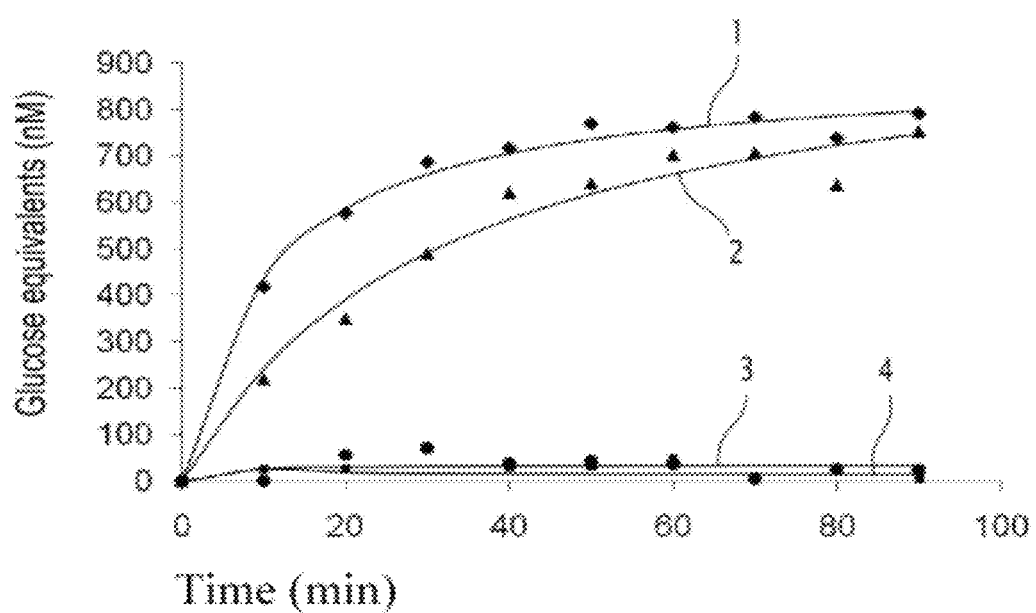
FIG.2

```
PorA (SEQ ID NO: 2)   1  MRKVLHHLI----FLVSANLSAQLESPTNG----------KKWEKVEQLSDEF    39
                         ::..::||    ::|:::::..:|.|::           ::::::||::||
PorB (SEQ ID NO: 5)   1  MKLSMQFLITILLITSITEAQEAFHFKPGEDFRQPHQEWKLIENMSDEF       50

PorA                 40  MGNSIETNKWYDYHPFWEGRAPSNFKKGNAFVSDGFLNLRSTLRKEPSSV       89
                         :|:::||.|:.::|:|||:|:|:||:|.||:|||:|::::|:|||:|:
PorB                 51  EGKKIDEKKWQISGQGWIGRAFGLFLAENIGLNNGSLQITTTMLPEPIVK      100

PorA                 90  QBPFKDIWVDAAAAVSKTEAQEGYYYEAREKASSLSMTSSFWF--------R   133
                         :: ::||::|::|.|::::||:.|.::|:::|:::::|::|:
PorB                103  NN------KTYTHGGYVGSRNGMTYGYYECEMKANKTFMSSTFWLINEGKDR   147

PorA                134  VG-----QFSEIDVIEHIGNPSKEMRQDLPY-QYHVNTHYYGKHAGLQPLG   179
                         :: :    |::|::::||:::  ||::|       ::|||     :|::
PorB                148  LGCDKRTTELDIQESVGQIT--NDADWMKYFDQTMSNTHSRNI-----PEG   192

PorA                180  TEY---------KMPGRGRDMFYTYGFWWKSENELLFYENGKQVMRIVFR   220
                         :::          ::|:::::|:|||:|:|:|:||::|:|||::|:::
PorB                193  CEVENGSSSKGKAELGSKAYEDFHVYGYWWKSKDEIYFPLBGKMQSKYTPP   242

PorA                221  VFLBEE--LRMIFPT-EVFPFATAGVANIGLPKFENLRDNSKN-TMKVDW   266
                         :::::   :::||:  :|::
PorB                243  ADFDIEMYLRMVVETYDWNP-------------VPKDGMPGSKEIDRTTYNW   282

PorA                267  VRKVYKLVDGTAAEDSSDAPIGSYISLKKTQGDGKFVTGFKDGSQLWARGS   316
                         :::||:|::|
PorB                283  VRSWQLNDSKN                                          293

PorA                317  TVQSWSEFKVEKHPFKGGITBKANSNSKYVQVQGSDINKPVRAAGDFQGDW   366
PorB                294                                                       293
```

FIG.5

```
PorA  (SEQ ID NO: 2)367  EQFEWKSKGNGLVALKNVLTGKWLQAFWTENNAIIRPKGPVDNGWETFAW  416
PorB                294                                                     293
PorA                417  KKETSFTASTALSAQLETKTVDGIRVYPSFASETLTIEGVEGENGLRVFD  466
PorB                294                                                     293
PorA                467  STGNPVLKKEGILGRKERLNVSGLIKGNYLLRTGSGEQTWFQKN        510
PorB                294                                                     293
```

FIG. 6

PORPHYRANASES, AND USE THEREOF FOR HYDROLYZING POLYSACCHARIDES

CROSS REFERENCE TO RELATED APPLICATIONS

This application is a U.S. nationalization under 35 U.S.C. §371 of International Application No. PCT/FR2010/051530, filed Jul. 20, 2010, which claims priority to French application no. FR 0955070, filed Jul. 21, 2009. The disclosures set forth in the referenced applications are incorporated herein by reference in their entireties.

BACKGROUND

The present invention relates to the isolation and the characterization of two proteins having novel enzymatic activity, i.e. a porphyranase activity. These proteins are useful for hydrolyzing polysaccharides containing sulfated agaro-colloids and for producing oligo-porphyrans, notably oligo-porphyrans of defined structure and size.

Polysaccharides such as agars (agarose, porphyran, etc.) and carrageenans are very widely used as gelling agents or thickeners in various business sectors, notably in the agri-food and cosmetic industry. Thus, about 6,000 tons of agars and 22,000 tons of carrageenans are yearly extracted from red seaweed for agri-food purposes. The agars industrially produced from red algae of the genera *Gelidium* and *Gracilaria*. Moreover, the red alga *Porphyra* (known under the common name of nori) is the most consumed alga worldwide. The yearly production is estimated to be 90,000 tons/year (dry weight), representing a market of about 1.5 billion US dollars.

Polysaccharides and their derivatives are also of interest in the therapeutic field. Thus, enoxaprin (Lovenox®), which is marketed for treating thromboembolic disorders, is a mixture of chains of sulfated polysaccharides with variable lengths and formed with recurrent disaccharide units. Moreover, certain polysaccharide and oligosaccharide sulfates, such as oligo-fucan sulfates produced from algal polysaccharides, are useful as anti-microbial and/or anti-viral agents in humans (Ghosh et al. 2009 Glycobiology. 19:2-15).

Agaro-colloids are complex polysaccharides. Certain species of algae contain an agaro-colloid given as a majority compound, such as for example the alga *Porphyra*, which contains as main constituent the agaro-colloid called porphyran. Misnomeringly, polysaccharides extracted from red algae are sometimes also designated as porphyran, although this is in fact a mixture of agarose and of porphyran, porphyran being the majority compound.

The base disaccharide unit forming porphyran consists of a D-galactose unit (unit G, see FIG. 1) bound in β-1,4 to an L-galactose unit modified by O-sulfatation in position O6 (unit L6S, see FIG. 1). The disaccharide units are then connected together through α-1,3 bonds. This sulfated polysaccharide is commonly considered as the precursor of agarose. In a natural medium, other chemical modifications such as methylation, give rise to even more variations of this basic structure. These chemical modifications have the consequence of modulating the gelling nature of the polymer.

Up to now, enzymes capable of degrading agars are known and mainly used: α-agarases and β-agarases. β-agarases act on the β-1,4 bond (Jam et al. Biochem J. 2005 385:703-13) and α-agarases on the α-1,3 bond (Flament et al. Appl. Environ. Microbiol. 2007 73:4691-94) of the agarose disaccharide unit, and these enzymes are specific of the non-substituted or non-modified units. Indeed, there exist many bacteria, essentially marine bacteria which produce enzymes capable of hydrolyzing agars (Michel at al., Appl. Microbiol. Biotechnol. 2006 71:23-33). Several genes of β-agarases have already been cloned from these microorganisms, and the corresponding proteins over-expressed and purified.

More particularly, the first fully biochemically and structurally characterized β-agarases are produced by a bacterial strain isolated from the red alga *Delesseria sanguinea* (Jam et al. Biochem. J. 2005 385:703-13, Allouch et al. J. Biol. Chem. 2003 278:47171-80). This bacterial strain was deposited at the DSMZ (Deutsche Sammlung von Mikroorganismen and Zelikulturen GmbH) collection on May 8, 1998 under number DSM 12170. Taxonomic identification of this strain shows that it defines a new genus in the class of Flavobacteria and its characterization earned it the name of *Zobellia galactanivorans* (Barbeyron et al. Int. J. Syst. Evol. Microbiol. 2001 51:985-97). κ-carrageenase of this marine bacterium was also cloned and characterized (Barbeyron et al. Mol. Biol. Evol. 1998 15:528-37).

On the other hand, no specific enzyme of sulfated polysaccharides such as porphyran has yet been described to this day.

Misnomeringly, certain enzymes capable of degrading polysaccharides extracted from red algae containing porphyran were incorrectly designated as porphyranases in the scientific literature. However, these enzymes actually have agarase activity and degrade the agars present in the polysaccharides extracted from red algae.

Thus, Lee et al. (2006 Annual Meeting and International Symposium of the Korean Society for Microbiology and Biotechnology) describe the cloning and the sequencing of an enzyme of *Vibrio pelagius*, which is called porphyranase. However, this enzyme hydrolyzes D-galactoside β-1,4 bonds and leads to the obtaining of oligo-agroses, such as neoagarotetraose, neoagarohexaose and neoagarooctaose. It therefore has agarase activity and not porphyranase activity.

Similarly, Hatada et al. (2006 J. Agric. Food Chem. 54:9895-9900) mention β-agarases and indicate that the latter would have a <<porphyranase>> activity. However these enzymes are described of being capable of hydrolyzing D-galactoside β-1,4 bonds and of leading to the obtaining of agarose oligomers. These enzymes are therefore actually agarases and not porphyranases.

Also, Aoki et al. (2002 Marine and Highland Bioscience Center Report, 14:33-41) describe the cloning of a gene coding for a so-called porphyranase of *Pseudomonas* sp. ND 137. However, the fact that the corresponding protein degrades porphyran has never been demonstrated, and its strong sequence identity (40%) with the agarase of *Pseudomonas* sp. CY24 proves the contrary. In fact, the sequence of the protein cloned by Aoki et al. is annotated as an agarase and not as a porphyranase in entry number BAB79291.1 of the NCBI data base.

Certain degradation products of porphyran (oligo-porphyrans) were able to be obtained by chemical hydrolysis (Zhao et al. 2006 Int. J. Biol. Macromol. 38:45-50). This method however leads to the obtaining of a highly heterogeneous mixture of oligo-porphyrans. Further, hydrolysis is complete and the average molecular weight of the obtained mixture remains high.

Therefore there is a need for enzymes capable of catalyzing the hydrolysis of sulfated polysaccharides such as porphyran, and this in order to obtain novel agents which may be used in the agri-food, cosmetic and/or pharmaceutical industry.

BRIEF DESCRIPTION OF THE FIGURES

FIG. 2: Enzymatic activity of porphyranases A and B. A) Enzymatic activity on agarose gel. 1 µg of the different agarases and porphyranases is deposited on a 1% agarose gel plate and incubated overnight at 30° C. The activity is then revealed by staining with lugol, indicated by the appearance of a light halo on a black background. A: β-agaraseA, B: β-agaraseB, C: β-agaraseD, D: β-porphyranaseA, E: β-porphyranaseB. B) Kinetic analysis of the digestion of porphyran. The porphyran was digested beforehand with a β-agarase, and only contained disaccharide units of the porphyran type. The lines show the digestion kinetics of PorA_CM (1), PorB (2), agaA (3) and agaB (4) of Z. galactanivorans.

FIGS. 5 and 6: Alignment of the sequences between PorA (SEQ ID NO: 2) and PorB (SEQ ID NO: 5). The arrow indicates the C-terminal end of PorA_CM.

DESCRIPTION OF THE SEQUENCES FROM THE LISTING OF SEQUENCES

Figure 1:
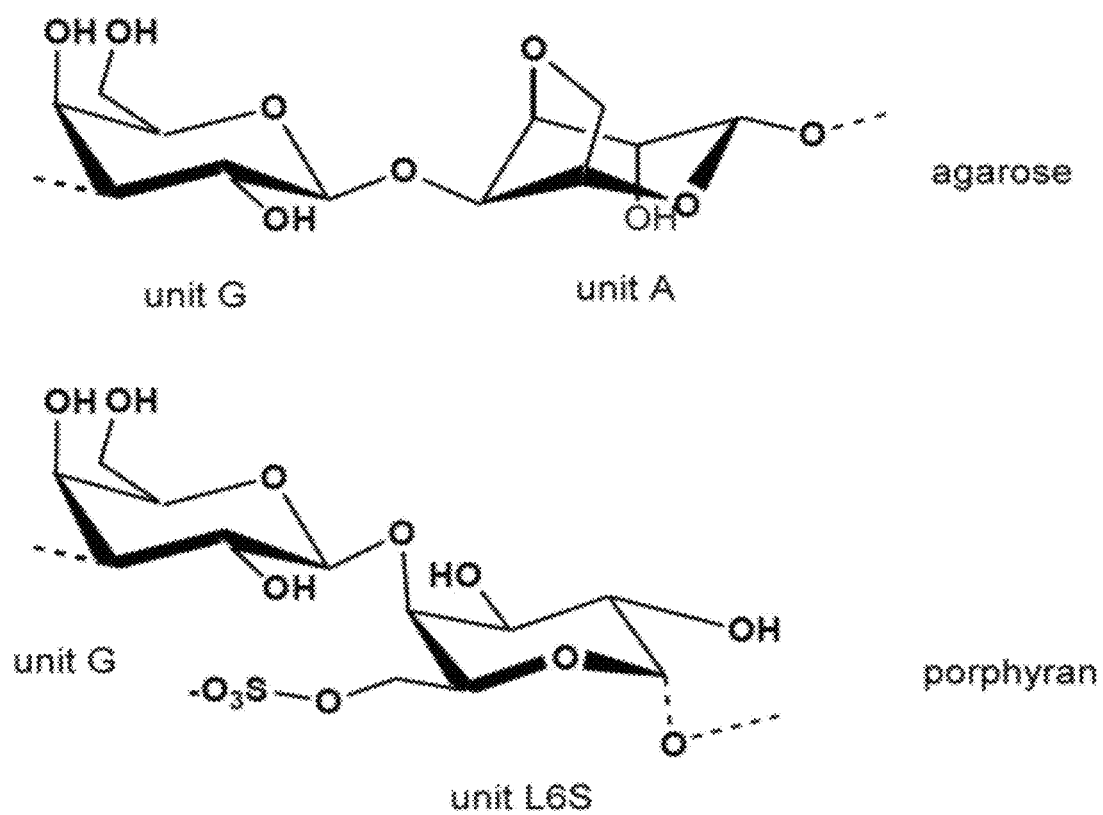
FIG. 1: Schematic presentation of the disaccharide units of agarose and of porphyran.

SEQ ID NO: 1 illustrates the nucleotide sequence of porphyranase A.

SEQ ID NO: 2 illustrates the protein sequence of porphyranase A.

SEQ ID NO: 3 illustrates the protein sequence of the recombinant porphyranase A produced in Example 2.

SEQ ID NO: 4 illustrates the nucleotide sequence of porphyranase B.

SEQ ID NO: 5 illustrates the protein sequence of porphyranase B.

SEQ ID NO: 6 illustrates the protein sequence of the recombinant porphyranase B produced in Example 2.

SEQ ID Nos: 7 to 10 illustrate primers which are suitable for cloning the genes coding for porphyranase A and porphyranase B.

DETAILED DESCRIPTION

The inventors have isolated and characterized the first two porphyranases described to this day. Although belonging to the family of GH16 of glycoside hydrolases, they have less than 26% sequence identity with the other members of this family present in Z. galactanivorans.

These porphyranases, designated as PorA and PorB, were cloned from Z. galactanivorans. PorA and PorB are illustrated by the sequences SEQ ID NO: 2 and SEQ ID NO: 5 respectively. The catalytic domain of PorA is 26.9% identical to that of PorB.

It was demonstrated that proteins PorA and PorB have β-porphyranase activity and they are without any agarase activity. An enzyme having such enzymatic activity had never yet been described.

It was also demonstrated that the proteins PorA and PorB may be used for hydrolyzing porphyran and allow to obtain oligosaccharides of defined structure and size. More particularly, PorA and PorB allow to obtain homogeneous mixtures of neo-porphyrobiose, neo-porphyrotetraose and/or neoporphyrohexaose.

Polypeptides According to the Invention

The inventors have isolated and characterized the first porphyranases described to this day. Consequently, the present invention relates to an isolated polypeptide characterized in that it has porphyranase activity.

Within the scope of this invention, by <<polypeptide>> is meant a molecule comprising a linear chain of amino acids bound together with peptide bonds.

By <<isolated>> polypeptide (or nucleic acid) is meant herein a polypeptide (or nucleic acid) isolated from the organism or the microorganism in which said polypeptide (or nucleic acid) is naturally present. In a preferred embodiment, the polypeptide or the nucleic acid is in an isolated and purified form. In a particular preferred embodiment, the isolated polypeptide is a recombinant polypeptide.

By <<porphyran>>, is meant herein the molecule consisting of a linkage of disaccharide units consisting of a D-galactose unit bound in β-1,4 with an L-galactose unit modified by O-sulfatation in the position O6.

By <<porphyranase activity>>, is meant herein the capability of catalyzing hydrolysis of porphyran. More particularly, the porphyranase activity of the polypeptides according to the invention consists in β-porphyranase activity, i.e. the capability of catalyzing the cleaving of the β-1,4 bonds between the D-galactose (<<unit G>> in FIG. 1) and the sulfated L-galactose unit in position 6 (<<unit L6S>> in FIG. 1) of the disaccharide unit of porphyran.

Porphyranase activity may for example be measured by obtaining kinetics of the digestion of porphyran. Such kinetics may for example be obtained as described in Example 3. More particularly a solution containing 1% (w/v) polysaccharide digested beforehand by a β-agarase may be used. 50 mL of the polysaccharide solution may be for example be incubated at 30° C. with 6 µg of enzyme. Aliquots may be taken all along the hydrolysis until complete hydrolysis is achieved. Digestion of porphyran by a porphyranase leads to the obtaining of oligo-porphyrans.

The polypeptides according to the invention are preferentially without any agarase activity. In other words, these polypeptides specifically catalyze hydrolysis of sulfated polysaccharides. The absence of an agarase activity may easily be measured, for example on a gel comprising 1% agarose (See FIG. 2). 1 µg of enzyme may for example be deposited on such a gel. After one night of incubation at 30° C., the agarase activity may be revealed by staining with lugol.

In a preferred embodiment, the polypeptide according to the invention comprises or consists in a sequence selected from:
- the residues 19 to 274 of the sequence SEQ ID NO: 2 (which correspond to a fragment of PorA comprising the catalytic domain, fragment designated as PorA CM);
- The residues 19 to 510 of the sequence SEQ ID NO: 2 (which correspond to the mature protein PorA);
- The residues 1 to 510 of the sequence SEQ ID NO: 2 (which correspond to the complete protein PorA);
- The residues 22 to 293 of the sequence SEQ ID NO: 5 (which correspond to the mature protein PorB); or
- The residues 1 to 293 of the sequence SEQ ID NO: 5 (which correspond to the complete protein PorB).

The polypeptides according to the invention also include polypeptides derived from proteins PorA and PorB of sequence SEQ ID NO: 2 or 5, it being understood that these derived polypeptides retain porphyranase activity. Such derived polypeptides comprise or consist in a sequence selected from:
a) a sequence at least 26, 30, 40, 50, 60, 70, 80, 90, 95, 96, 97, 98 or 99% identical to the residues:
  19 to 274 of the sequence SEQ ID NO: 2;
  19 to 510 of the sequence SEQ ID NO: 2;
  1 to 510 of the sequence SEQ ID NO: 2;
  22 to 293 of the sequence SEQ ID NO: 5; or
  1 to 293 of the sequence SEQ ID NO: 5.

b) a fragment of at least 20, 50, 100, 150, 200, 210, 220, 230, 240 or 250 consecutive amino acids of sequence (a); and
c) a fragment of at least 20, 50, 100, 150, 200, 210, 220, 230, 240 or 250 consecutive amino acids of a sequence consisting in the residues:
  19 to 274 of the sequence SEQ ID NO: 2;
  19 to 510 of the sequence SEQ ID NO: 2;
  1 to 510 of the sequence SEQ ID NO: 2;
  22 to 293 of the sequence SEQ ID NO: 5; or
  1 to 293 of the sequence SEQ ID NO: 5.

By <<sequence at least 95% (for example) identical to a reference sequence>>, is meant a sequence identical with the reference sequence except that this sequence may include up to five point-like mutations (substitutions, deletions and/or insertions) for each portion of a hundred amino acids of the reference sequence. Thus, for a reference sequence with 100 amino acids, a fragment of 95 amino acids and a sequence of 100 amino acids including 5 substitutions with respect to the reference sequence are two examples of sequences 95% identical to the reference sequence.

The identity percentage is generally determined by using a software package for analyzing sequences. The program <<needle>>, which resorts to the global alignment algorithm <<Needleman-Wunsch>> for finding the optimum alignment (with gaps) of two sequences over the whole of their length, may for example be used. This program is notably available on the site ebi.ac.uk.

The derived polypeptides may differ from the reference sequence (in this case the sequence SEQ ID NO: 2 or 4 or one of its fragments) by the presence of mutations of the type: deletion, insertion and/or substitution of amino acids. The substitutions may be conservative or non-conservative substitutions.

In a particular embodiment, the derived polypeptides differ from the reference sequence only by the presence of conservative substitutions. Conservative substitutions are substitutions of amino acids of the same class, such as substitutions of amino acids at the non-charged side chains (such as asparagine, glutamine, serine, cysteine, and tyrosine), of amino acids to the basic side chains (such as lysine, arginine and histidine), of amino acids to the acid side chains (such as aspartic acid and glutamic acid), of amino acid to the apolar side chains (such as alanine, valine, leucine, isoleucine, proline, phenylalanine, methionine and tryptophan).

The derived polypeptides may also correspond to allele variants of the proteins PorA or PorB of sequence SEQ ID NO: 2 or 4, to proteins homologous to PorA and PorB in other species such as *Zobellia galactanivorans*, or to fragments of such allele variants or homologous proteins retaining the porphyranase activity.

Optionally, the polypeptides according to the invention comprise a signal peptide. If a signal peptide is present, it may be the native signal peptide of the protein (i.e. the residues 1 to 18 of SEQ ID NO: 2 for PorA, and the residues 1 to 21 of SEQ ID NO: 5 for PorB). Alternatively, the signal peptide may be a signal peptide heterologous to PorA or PorB, for example a signal peptide suitable for expressing the mature protein PorA or PorB in a given host cell. The sequences SEQ ID Nos: 2, 3, 5 and 6 are examples of polypeptides according to the invention either comprising a native signal peptide (SEQ ID Nos: 2 and 5), or a heterologous signal peptide (SEQ ID Nos: 3 and 6).

The polypeptides according to the invention may be prepared by purification from their original organism or microorganism, by chemical synthesis or genetic engineering and this by using techniques well known to one skilled in the art.

In a preferred embodiment, the polypeptides according to the invention are obtained by genetic engineering.

Nucleic Acids According to the Invention

The present invention also relates to an isolated nucleic acid coding for a polypeptide according to the invention. This polypeptide according to the invention may correspond to any of the porphyranases described in the previous paragraph.

The term <<nucleic acid>> designates both DNA molecules and RNA molecules and notably includes cDNA molecules and mRNA molecules. The nucleic acid may be in the double strand form (for example in the case of a nucleic acid comprised in an expression vector) or in a single strand form (for example in a case of probes or primers).

More particularly, the nucleic acid according to the invention may comprise or consist in a sequence selected from:
  a) nucleotides 1 to 1533 or 55 to 1533 of the sequence SEQ ID NO: 1;
  b) nucleotides 1 to 882 or 64 to 882 of the sequence SEQ ID NO: 4; and
  c) a sequence complementary to the sequence (a) or (b).

The nucleic acid according to the invention may also comprise or consist in sequences derived from the sequences SEQ ID NO: 1 or 4. The derived nucleic acids include nucleic acids for which the sequences comprise or consist in a sequence selected from:
  a) a sequence at least 30, 40, 50, 60, 70, 80, 90, 95, 96, 97, 98 or 99% identical to the nucleotides:
    1 to 1533 or 55 to 1533 of the sequence SEQ ID NO: 1; or
    1 to 882 or 64 to 882 of the sequence SEQ ID NO: 4.
  b) a fragment of at least 60, 150, 300, 450, 600 or 750 consecutive nucleotides of sequence (a);
  c) a fragment of at least 60, 150, 300, 450, 600 or 750 consecutive nucleotides of a sequence consisting in the nucleotides:
    1 to 1533 or 55 to 1533 of the sequence SEQ ID NO: 1; or
    1 to 882 or 64 to 882 of the sequence SEQ ID NO: 4.
  d) a sequence coded by a nucleic acid which hybridizes to the sequence SEQ ID NO: 1 or 4 under strong stringency conditions; and
  e) a sequence complementary to one of sequences (a) to (d).

The identity percentage between two nucleotide sequences is determined in the same way as the identity percentage between two sequences of amino acids.

The <<strong stringency conditions>> are conditions known to one skilled in the art, and may for example correspond to conditions for hybridizations on DNA bound to a filter in a 5× sodium citrate salt buffer (SSC), 2% sodium dodecyl sulfate (SDS) 100 micrograms/mL of single strand DNA, at 55-65° C. for 8 hours and washing in 0.2×SSC and 0.2% SDS at 60-65° C. for 30 minutes.

The sequences of the derived nucleic acids may include mutations such as substitutions, deletions and/or insertions of nucleotides. The substitutions may either be silent, or may lead to mutations at the protein coded by the nucleic acid. Preferably, the substitutions, deletions and/or insertions at the nucleotide sequence do not lead to a change in reading phase, nor to the introduction of a stop-codon.

In a preferred embodiment, the derived nucleic acid is a nucleic acid coding for the mature or complete protein PorA of sequence SEQ ID NO: 2, for the mature or complete protein PorB of sequence SEQ ID NO: 5, or for fragments thereof retaining the porphyranase activity, but the nucleotide sequence of which differs from the sequence SEQ ID NO: 1 or 4 because of degeneration of the genetic code and/or because of an allele variation.

Another particular preferred embodiment deals with nucleic acids coding for homologous proteins of PorA or PorB in species other than *Zobellia galactanivorans*, or fragments thereof retaining the porphyranase activity.

Another aspect of the invention deals with nucleotide probes and primers comprising or consisting in a fragment of SEQ ID NO: 1 or SEQ ID NO: 4. Such probes and primers may for example comprise or consist in 15 to 50 consecutive nucleotides, preferentially 18 to 35 consecutive nucleotides, of SEQ ID NO: 1 or SEQ ID NO: 4. Such probes and primers do not code for a polypeptide according to the invention but are useful for cloning, sequencing and/or detecting nucleic acids according to the invention. The probes may optionally be labeled, for example by means of a radioactive marker or a fluorophore. Moreover, the probes and primers may comprise in addition to a fragment of the sequence SEQ ID NO: 1 or SEQ ID NO: 4, a heterologous sequence such as the sequence of a restriction site or a sequence for binding to a marker.

The nucleic acids according to the invention may be prepared by chemical synthesis or genetic engineering by using techniques well known to one skilled in the art and described i.a. in Sambrook et al. ("Molecular Cloning: a Laboratory Manual" Ed. Cold Spring Harbor Press, N.Y., 1989). The nucleic acids according to the invention may for example be obtained by amplification of the genes of *Zobellia galactanivorans* by means of the PCR (Polymerase Chain Reaction) method, as described in Example 1. The thereby amplified fragment of nucleic acids may then be cloned into an expression vector according to the techniques described in Maniatis. (<<Molecular Cloning. A Laboratory Manual>> New York, 1982) and/or in Example 1.

Expression Vectors and Host Cells According to the Invention

The invention also relates to expression vectors comprising a nucleic acid according to the invention. These expression vectors which may for example be plasmids, include, in addition to the nucleic acid sequence according to the invention, means required for its expression. These means may for example include a transcription terminator or promoter. The expression vector may also include other elements such as a replication origin, a multiple cloning site, an enhancer, a signal peptide which may be fusioned in phase with the polypeptide of the invention during cloning, and one or more selection markers.

Another aspect of the invention deals with a host cell transformed by an expression vector or a nucleic acid according to the invention.

The host cell may be a prokaryotic cell or an eukaryotic cell. Currently used host cells for expressing recombinant cells notably include cells of bacteria such as *Escherichia coli*, yeast cells such as *Saccharomyces cerevisiae*, fungi cells such as *Aspergillus niger*, insect cells and mammal cells (notably human cells) such as the cell lines CHO, HEK 293, PER-C6, etc.

The transformation of prokaryotic cells and of eukaryotic cells is a technique well known to one skilled in the art. Depending on the cell to be transformed, one skilled in the art may easily determine the means required for introducing and expressing the nucleic acid according to the invention, in the selected host cell. Thus, the expression vector and the method for introducing the expression vector within the host cell will be selected depending on the selected host cell.

The host cell transformed by an expression vector or a nucleic acid according to the invention preferentially expresses the polypeptide according to the invention in a stable way. One skilled in the art may easily check that the host cell expresses the polypeptide according to the invention in a stable way, for example by using the Western Blot technique.

The host cells according to the invention are notably useful for producing polypeptides according to the invention. The invention therefore relates to a method for producing a polypeptide according to the invention comprising the step of cultivating a host cell according to the invention under conditions allowing expression of the said polypeptides according to the invention. This method may further comprise a step for purifying said polypeptide according to the invention. The cultivation and purification steps may for example be accomplished as described in Example 2.

Methods for Hydrolysis of Polysaccharides According to the Invention

The inventors have found that the enzymes PorA and PorB may be used for hydrolyzing porphyran, and allow oligosaccharides to be obtained with a defined structure and size. More particularly, by hydrolysis of porphyran by PorA and PorB it is possible to obtain oligo-porphyrans, notably neo-porphyrobiose, neo-porphyrotetraose and/or neo-porphyrohexaose.

An aspect of the invention therefore deals with the use of a polypeptide according to the invention for hydrolyzing polysaccharides and/or for producing oligosaccharides.

The polysaccharides used with the scope of this method are polysaccharides which may contain sulfated polysaccharides, which may either be the majority compound of said polysaccharide or not. Preferentially, the polysaccharides used within the scope of this method comprise or consist in porphyran. Alternatively, the polysaccharides used within the scope of this method may comprise or consist in a polysaccharide different from porphyran but at least partly consisting of disaccharide units consisting of a D-galactose unit bound in β-1,4 with an L-galactose unit modified by O-sulfatation in position O6.

Such polysaccharides are present in marine plants. They may for example be obtained from marine plants, and in particular from red algae, by using extraction procedures well known to one skilled in the art, such as the technique described by Morrice et al. (Eur. J. Biochem. 1983 133:673-84). They may optionally be separated from the other possible components by liquid chromatography methods.

In a preferred embodiment, the invention deals with the use of a polypeptide according to the invention for hydrolyzing porphyran and/or for producing oligo-porphyrans, notably neo-porphyrobiose, neo-porphyrotetraose and/or neo-porphyrohexaose.

The invention also relates to a method for hydrolyzing polysaccharides and/or producing oligosaccharides comprising the following steps:

a) providing a polypeptide according to the invention or a host cell according to the invention; and
b) putting said polypeptide or cell host in contact with a polysaccharide under conditions leading to the obtaining of hydrolyzed polysaccharides, for example under conditions leading to complete hydrolysis.

As this is clearly apparent from reading the present application, in a preferred embodiment, the method for hydrolyzing polysaccharides and/or producing oligosaccharides according to the invention consists in a method for hydrolyzing porphyran and/or producing oligo-porphyrans, notably neo-porphyrobiose, neo-porphyrotetraose and/or neo-porphyrohexaose. The conditions leading to the obtaining of hydrolyzed polysaccharides may easily be determined by one skilled in the art. For example, the conditions described in Example 3 may be used. The polypeptide or host cell may for example be put into contact with the polysaccharide at a temperature of 30° C. During this contacting, 6 μg of polypeptide may for example be added to 50 mL of a solution containing 1% (w/v) polysaccharide. The incubation time will be adjusted depending on the hydrolyzed polysaccharide which one wishes to obtain. The incubation may for example last for about or at least 6, 10 or 14 hours. Thus, starting with a polysaccharide solution containing porphyran, it will be possible to obtain the following oligosaccharides depending on the incubation time: neo-porphyrobiose, neoporphyrotetraose and/or neo-porphyrohexaose.

The method according to the invention may optionally comprise a step (c) for purifying said hydrolyzed polysaccharides. Techniques for purifying hydrolyzed polysaccharides are well known to one skilled in the art. The purification may for example be achieved by exclusion chromatography, as described in Example 4. The sample containing the oligosaccharides may for example be eluted with 50 mM ammonium carbonate at a rate of 1.5 mL/min for 650 minutes.

In a preferred embodiment, the hydrolyzed polysaccharides obtained by the method according to the invention have an average molecular weight ($M_w$) less than or equal to 5800, 5500, 5000, 4500, 4000, 3500 or 3000 Da, further preferentially less than or equal to 5800 Da. Preferentially, the hydrolyzed polysaccharides obtained by the method according to the invention have a lower molecular weight of 1,270, 1,170, 850, 750 or 425 Da, for example about 1,261.04, 1,163.97, 840.69, 743.62 or 420.344 Da.

In another preferred embodiment, the hydrolyzed polysaccharides obtained by the method according to the invention comprise at least 25%, 50%, 60%, 70%, 80%, 90%, 95% or 99% of one or more oligo-porphyrans selected from neo-porphyrobiose, neo-porphyrotetraose and neo-porphyrohexaose.

By <<neo-porphyrobiose>>, is meant the disaccharide unit of porphyran (which is illustrated in FIG. 1). By <<neo-porphyrotetraose>>, is meant a linkage of two disaccharide units of porphyran. By <<neo-porphyrohexaose>>, is meant a linkage of three disaccharide units of porphyran.

The thereby hydrolyzed and purified polysaccharides may then be formulated as an agrifood, cosmetic or pharmaceutical composition.

Finally, the invention also deals with hydrolyzed polysaccharides in particular oligo-porphyrans, notably neo-porphyrobiose, neo-porphyrotetraose and/or neo-porphyrohexaose, which may be obtained by the method according to the invention, and with agrifood, cosmetic and pharmaceutical compositions containing such hydrolyzed polysaccharides.

The contents of the publications, articles, handbooks, patents and patent applications cited in this text are incorporated to the present text by reference.

The invention will now be described in detail by means of the experimental discussion hereafter, which illustrates the invention without limiting the scope thereof.

EXAMPLES

Example 1

Cloning of the Genes of Porphyranase A and B

The open reading frames coding for the enzymes PorA and PorB were built on the basis of sequences of the genome of *Z. galactanivorans*. The target genes were amplified in parallel by PCR, from genomic DNA material of *Z. galactanivorans*, with 5' and 3' primers as indicated in Table 1 below.

TABLE 1

Sequence of the primers for the cloning of PorA_CM and PorB, calculated in order to obtain a Tm of ~70° C.

| Name | SEQ ID NO: | Sequence |
|---|---|---|
| | | 5' primer |
| PorA_CM | 7 | ggggggggATCCCAATTACCATCTCCTACAAACGGG |
| PorB | 8 | ggggggggATCCCAAGAAGCTCCACATTTTAAGCCTG |
| | | 3' primer |
| PorACM | 9 | CCCCCCgAATTCTTAGTCAACCAATTTATACACCCGTACC |
| PorB | 10 | CCCCCCgAATTCTTAATTCTTTGAATCAACCAATTGCCATG |

The entire gene of β-porphyranase A (containing the catalytic domain and the two domains resembling modules for binding to the substrate) was truncated in order to produce a recombinant protein only containing the catalytic domain (residues 19-275), which will be called subsequently PorA_CM. PorB, the sequence of which indicates a single module belonging entirely to the family GH16, was entirely cloned in order to obtain the active recombinant protein.

The products of the PCR amplification were then purified with the Qiaquick PCR kit and eluted with 50 µl of $H_2O$. The purified PCR products were in turn digested for three hours at 37° C. with the mixture of restriction enzymes BgIII/EcoRI in their respective buffers (NEB2 and BioLabs). After digestion, the products were purified with the Qiaquick PCR kit and then eluted with 25 µl of $H_2O$. The PCR products were subject to ligation with the vector PFO4 (derived from the vector pet15), dephosphorylated beforehand and digested with adequate restriction enzymes. This ligation procedure was carried out with T4 DNA ligase at 4° C. overnight.

For the transformation procedure, *E. coli* (strain DH5α) cells made competent via a chemical route, were used. For this, the cells were put onto an ice, water and NaCl mixture for 30 minutes, and were then incubated for 30 minutes with the mixture resulting from the ligation. The transformation was carried out by applying a thermal shock for 45 secs at 42° C., and the cells were then put back into the ice, water and NaCl mixture for 30 minutes.

Example 2

Expression and Purification of the PorA CM and PorB

PorA_CM and PorB were over-expressed in *E. coil* cells (strain BL21, DE3). The overexpression was carried out at 20° C. in 1 L of a ZYP-5052 medium with 100 µg $mL^{-1}$ of ampicillin (Studier 2005 Protein Expr. Purif. 41(1):207-34). The cells were harvested by centrifugation (4,000 g, 20 min, 4° C.) after 3 days and a half of cultivation, (final OD at 600 nm: about 16). The pellet was then suspended in buffer A (20 mM Tris pH 8, 200 mM NaCl, 20 mM imidazole, pH 7.5, lysozyme, DNAse). The thereby suspended cells were lyzed with lysozyme for 30 minutes on ice, and were then subject to sonication. The lyzate was clarified by centrifugation (50,000 g, 30 min, 4° C.), and then by filtration by using 0.2 µm filters (Millipore). The thereby filtered solution was loaded on a 10 mL IMAC HyperCell (Pall Corporation) column, which was filled with an $NiSO_4$ solution. The column had been equilibrated beforehand with the buffer A, without any lysozyme and DNAse. After a step for washing with the buffer A (ten column volumes), the protein was eluted at 1 mL·$min^{-1}$, in 60 mL by producing a linear gradient between the buffer A and a buffer A added with 60% of buffer B (20 mM Tris pH 8, 200 mM NaCl and 500 mM imidazole). The proteins were concentrated by ultra-filtration on an Amicon membrane (polyethersulfone, limiting size 30 kDa), in order to obtain a final volume of about 5 mL. A second purification step was then carried out on a Sephacryl S-200 (GE Healthcare) column pre-equilibrated with a buffer C (20 mM Tris pH 8, 4% (v/v) glycerol for PorA_CM, and 20 mM Tris for PorB) at a rate of 1 mL·min$^{-1}$. All the fractions containing the pure protein (as analyzed with SDS-PAGE) were added and concentrated by filtration/centrifugation (Amicon, limiting size 10 kDa) at 2.6 mg/mL for PorA_CM and about 8 mg/mL for PorB. All the chromatography procedures were carried out with an ÄKTA Explorer system (GE-Healthcare) at room temperature.

Example 3

Enzymatic Degradation of the Porphyran

A solution containing 1% (w/v) of the polysaccharide was used for enzymatic hydrolysis with porphyranases A and B. A total of 50 mL of the polysaccharide solution was incubated with 6 µg of enzyme at 30° C. for one night. Aliquots were taken all along the hydrolysis until complete hydrolysis is achieved (about 14 hours).

After complete digestion by the enzyme, the solution was heated to 96° C. for 30 min in order to inactivate any possible residual activity of the enzyme. The solution was then centrifuged for 20 min at 5,000 g and at 4° C. and the supernatant was filtered with 0.2 µm Millipore syringe filters. The digested polysaccharide was frozen at −80° C. and then freeze-dried.

The aliquots were analyzed by the method for detecting reducing sugars by mixing 10 µl of protein aliquot with 90 µl of water (10× dilution), and then with 1 mL of the ferricyanide solution (300 mg potassium hexocyanoferrate III, 29 g Na$_2$CO$_3$, 1 mL of 5 M NaOH, completed to 1 L with water). The mixture was heated to 100° C. for 15 mins, and then cooled to room temperature in order to measure the absorbance at 420 nm.

Example 4

Purification of the Oligo-Porphyrans by Preparative Exclusion Chromatography

Purification of the oligo-porphyrans was carried out by preparative exclusion chromatography with three Superdex 30 (26/60) columns from GE HealthCare in series, integrated on an injector system/liquid collector HPLC system (Gilson). The oligosaccharides were detected by their refractive index (Spectra System RI-50 detector) and the integration of the data (Gilson and refraction detector) by the software package Unipoint (Gilson).

The frozen and freeze-dried polysaccharide digestion product was dissolved in demineralized water in order to obtain a 4% (w/v) solution. After filtration on a 0.45 µm porous membrane, 4 mL of the sample were injected and then eluted with 50 mM of ammonium carbonate [(NH$_4$)$_2$CO$_3$] at a rate of 1.5 mL/min for 650 minutes. The oligosaccharide fractions were collected and directly analyzed by HPLC.

Figure 3:
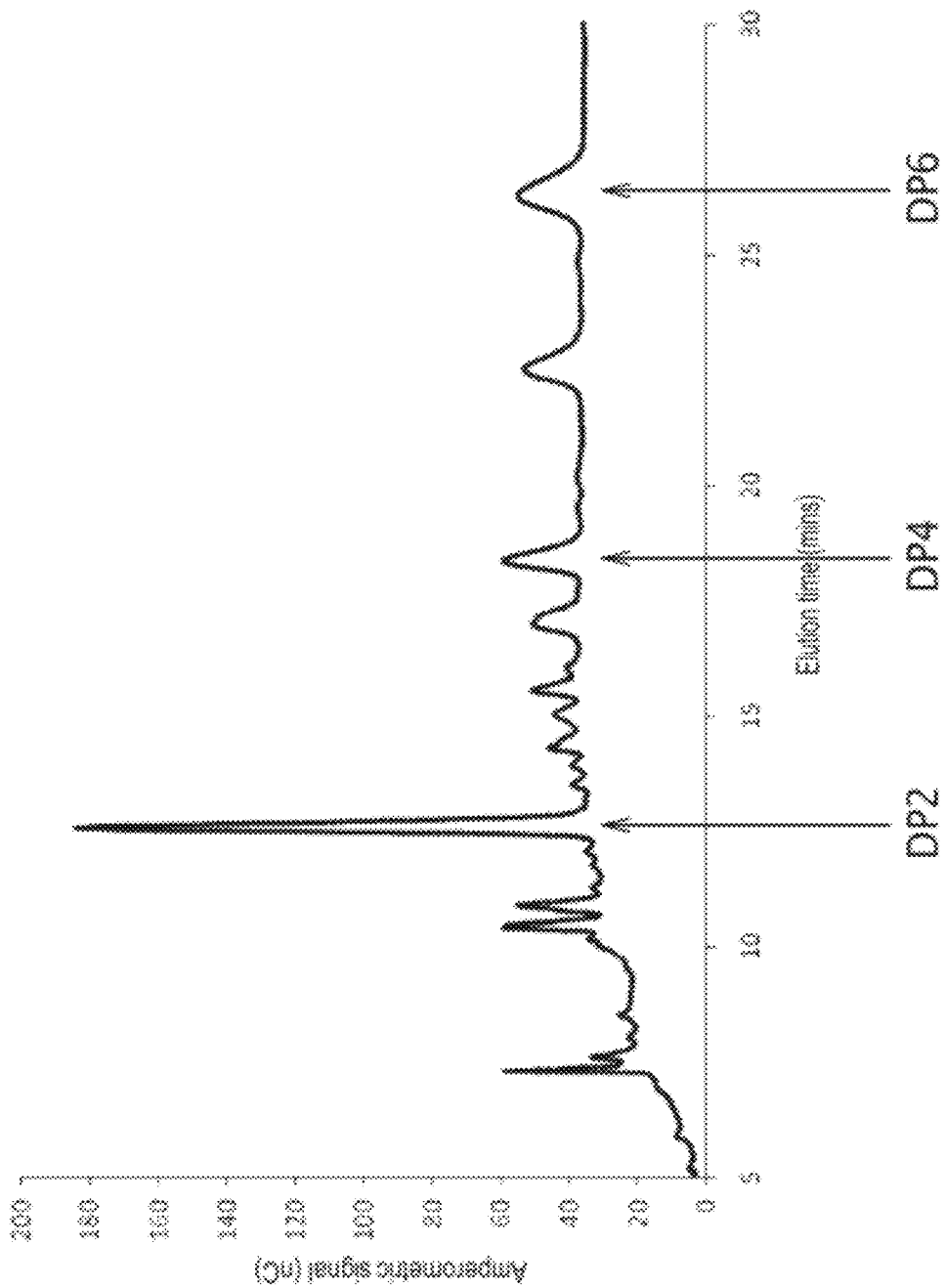
FIG. 3: Analysis by HPLC of the degradation products of the porphyran obtained with the enzyme PorA. DP2, DP4 and DP6 designate the di-, tetra- and hexa-saccharides, which were then analyzed by NMR.
Figure 4:
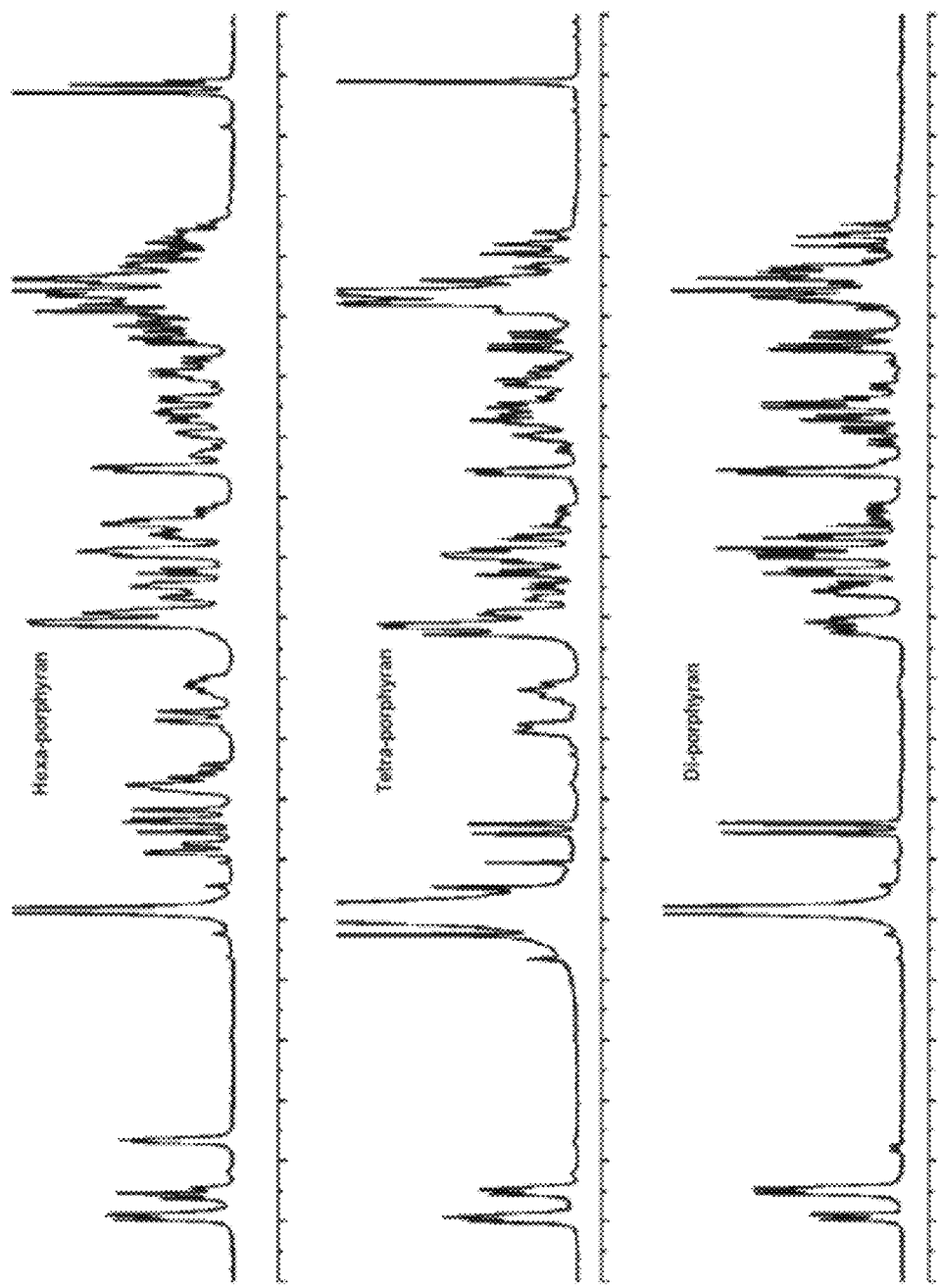
FIG. 4: $^1$H-NMR spectrum of neo-porphyro-bi-, tetra-, and hexa-oses, obtained with the enzyme PorA.

According to this method, it is possible to prepare oligosaccharides exclusively consisting of the recurrent porphyran unit or hybrid oligosaccharides containing porphyran units associated with units of the agarose type. Thus, we isolated and purified oligo-porphyrans from the disaccharide to the hexasaccharide (FIGS. 3 and 4), corresponding to the molecular weights of 420.344 Da (neo-porphyrobiose, called di-porphyran in FIG. 4), 840.69 and/or 743.62 Da (neo-porphyrotetraose, called tetra-porphyran in FIG. 4) and 1261.04 and/or 1163.97 Da (neo-porphyrohexaose, called hexa-porphyran in FIG. 4), respectively.

Example 5

Results and Discussion

The sequencing of the complete genome of the bacteria *Zobellia galactanivorans* (deposited at the SDMZ Collection on May 8, 1998 under number DSM 12170) was achieved. The sequencing allowed identification of sixteen genes belonging to the GH16 family of glycoside hydrolases. Among these sixteen genes, the genes coding for κ-carraghenase CgkA and β-agarases AgaA and AgaB are already known and characterized (Barbeyron et at Mol. Biol. Evol. 1998 15:528-37 ; Jam et al. Biochem. J. 2005 385:703-13; Allouch et al. J. Biol. Chem. 2003 278:47171-80).

Two other genes belonging to the GH16 family of glycoside hydrolases were cloned as discussed in Example 1 above. These genes called porA and porB, code for proteins designated as PorA and PorB respectively. The protein PorA consists of 510 amino acids and has a theoretical molecular mass of 57.311 kDa. After removing the signal peptide, this protein has a calculated molecular mass of 55.193 kDa. The protein PorB consists of 293 amino acids. After removing the signal peptide, this protein has a theoretical molecular mass of 31.271 kDa.

As shown in Table 2 below, both of these genes have less than 25% identity with the β-agarases and κ-carrageenase of *Zobellia galactanivorans*.

TABLE 2

Sequence identity matrix between catalytic modules of certain glycoside hydrolases of the GH16 family of *Zobellia galactanivorans*.

|  | 1 | 2 | 3 | 4 | 5 |
|---|---|---|---|---|---|
| 1. AgaA |  | 35.6 | 24.2 | 25.2 | 22.8 |
| 2. AgaB |  |  | 18.4 | 22.0 | 20.0 |
| 3. CgkA |  |  |  | 23.3 | 21.0 |
| 4. PorA |  |  |  |  | 26.9 |
| 5. PorB |  |  |  |  |  |

Once the cloning has been carried out, the proteins PorA and PorB were overexpressed in *Escherichia coli* as discussed in Example 2.

The activity of the proteins PorA and PorB on several galactans of red algae was then studied (Example 3). It was seen that these enzymes do not have any activity on the carrageenans or on agarose (FIG. 2A). On the other hand, these enzymes have strong activity on porphyran (FIG. 2B).

The purification of the oligosaccharides produced and their characterization by $^1$H NMR (Example 4) show that the enzymes PorA and PorB specifically hydrolyze the porphyran and cleave the β-1,4 bonds between the D-galactose units and the sulfated L-galactose units in position 6. Sulfatation is required for the activity of the enzyme and is exclusive with respect to β-agarase activities, as shown by the activity of PorA and PorB on porphyran, pre-digested by a β-agarase (FIG. 2B).

As shown in Example 4, the hydrolysis of the porphyran by PorA and PorB allow to obtain homogeneous mixtures of neoporphyrobiose, neo-porphyrotetraose and/or neo-porphyrohexaose.

Consequently, the proteins PorA and PorB are the first β-porphyranases described to this day.

The invention claimed is:

1. An isolated polypeptide having porphyranase activity and comprising an amino acid sequence having at least 90% amino acid sequence identity to the sequence of residues 19 to 274 of the amino acid sequence of SEQ ID NO: 2 or comprising an amino acid sequence having at least 90% amino acid sequence identity to the sequence of residues 22 to 293 of the amino acid sequence of SEQ ID NO: 5.

2. The polypeptide according to claim 1, wherein said polypeptide is a recombinant polypeptide.

3. An expression vector comprising an isolated nucleic acid encoding the isolated polypeptide according to claim 1.

4. An isolated host cell transformed by the expression vector according to claim 3.

5. A method for hydrolyzing polysaccharides comprising the following steps:

a) providing an isolated polypeptide having porphyranase activity and comprising an amino acid sequence having at least 90% amino acid sequence identity to the sequence of residues 19 to 274 of the amino acid sequence of SEQ ID NO: 2 or comprising an amino acid sequence having at least 90% amino acid sequence identity to the sequence of residues 22 to 293 of the amino acid sequence of SEQ ID NO: 5, or providing an isolated host cell transformed by an expression vector comprising a nucleic acid encoding a polypeptide having porphyranase activity and comprising an amino acid sequence having at least 90% amino acid sequence identity to the sequence of residues 19 to 274 of the amino acid sequence of SEQ ID NO: 2 or comprising an amino acid sequence having at least 90% amino acid sequence identity to the sequence of residues 22 to 293 of the amino acid sequence of SEQ ID NO: 5; and b) putting said polypeptide or said host cell in contact with a polysaccharide under conditions for hydrolyzing said polysaccharide to obtain hydrolyzed polysaccharides.

6. The method according to claim 5, further comprising a step (c) for purifying said hydrolyzed polysaccharides.

7. The method according to claim 6, further comprising a step (d) for formulating said hydrolyzed and purified polysaccharides in an agrifood, cosmetic or pharmaceutical composition.

8. The method according to claim 5, wherein said polysaccharide contains porphyran.

* * * * *

SEQUENCE LISTING

<160> NUMBER OF SEQ ID NOS: 10

<210> SEQ ID NO 1
<211> LENGTH: 1533
<212> TYPE: DNA
<213> ORGANISM: Zobellia galactanivorans
<220> FEATURE:
<221> NAME/KEY: sig_peptide
<222> LOCATION: (1)..(54)

<400> SEQUENCE: 1

| | | | | | | |
|---|---|---|---|---|---|---|
| atgaaaaaag | tattactatt | tttaattttt | ttagtaagcg | caaatctttc | tgcgcaatta | 60 |
| ccatctccta | caaacgggaa | gaaatgggaa | aaggttgaac | aattatccga | tgaatttaac | 120 |
| ggcaactcca | ttgacaccaa | taagtggtat | gattaccacc | cttttttggga | gggccgagcc | 180 |
| cccagcaatt | ttaaaaaagg | gaatgctttc | gtaagtgacg | gtttcctaaa | ccttcgttct | 240 |
| acattaagaa | aagaaccaag | tagcgttcaa | gatccttta | aggatatttg | ggtagatgct | 300 |
| gccgcggcgg | tttccaagac | caaggcccaa | cccggatatt | attacgaggc | tcgctttaag | 360 |
| gcctcctctt | tgtctatgac | ttcttcgttt | tggttccgcg | ttggccaatt | ttctgaaatc | 420 |
| gatgttatcg | agcatattgg | aaatccatcc | aaagaaaacc | gacaggacga | tcttccttat | 480 |
| caatatcatg | ttaatacaca | ttattacgga | aaacatgccg | gattgcaacc | acttggaacc | 540 |
| gaatataaaa | tgcccggcag | gggaagggat | aatttttaca | cctatggatt | ctggtggaag | 600 |
| agtcctaatg | aacttctttt | ttacttcaat | ggcaagcagg | ttatgcgtat | cgttccaaga | 660 |
| gtgcctttag | acgaggaatt | aagaatgatt | tttgacacag | aagtattccc | ttttgccacg | 720 |
| gcaggtgttg | ccaatatcgg | acttcctaag | ccggaaaacc | tccgtgacaa | ttctaaaaac | 780 |
| accatgaaag | tagattgggt | acgggtgtat | aaattggttg | acggcaccgc | cgcggaagac | 840 |
| agttccgatg | ctccgatcgg | cagttacatt | tccctcaaaa | aaacgcaagg | cgacggtaaa | 900 |
| tttgtaaccg | gtgaaaaaga | tggcagccaa | ttggttgcaa | gaggctcgac | cgttcaaagc | 960 |
| tgggaaaaat | tcaaagtaga | aaacacccct | aaaggcggga | ttacccttaa | ggccaattcc | 1020 |
| aatggtaaat | atgtacaagt | tcaaggaagc | gacatcaaca | aaccggtaag | ggccgcgggc | 1080 |
| gattttcagg | gcgattggga | acaattcgaa | tggaaatcca | aaggaaacgg | acttgtagcc | 1140 |
| ttgaaaaacg | tgcttacggg | caaatggcta | caggctccat | ggaccgaaaa | caacgcgata | 1200 |
| atccgaccga | agggcccgt | agataatggt | tgggaaactt | ttgcttggaa | aaaggagaca | 1260 |
| tcacctaccg | ccagtacggc | gctttccgcc | cagttggaga | caaagaccgt | agatggaata | 1320 |
| agagtgtatc | ccagccccgc | atcggaaacc | ttgactattg | agggagtgga | gggcgaaaat | 1380 |
| ggtttacgtg | tttttgactc | gacgggcaat | ccagtcctta | aaaagaagg | catactaggc | 1440 |
| cgtaaagaac | gattaaacgt | ttccggtctt | atcaaaggca | actacctatt | gcgcactgga | 1500 |
| tcaggtgaac | aaacctggtt | tcagaaaaac | tga | | | 1533 |

<210> SEQ ID NO 2
<211> LENGTH: 510
<212> TYPE: PRT
<213> ORGANISM: Zobellia galactanivorans
<220> FEATURE:
<221> NAME/KEY: SIGNAL
<222> LOCATION: (1)..(18)

<400> SEQUENCE: 2

```
Met Lys Lys Val Leu Leu Phe Leu Ile Phe Leu Val Ser Ala Asn Leu
1               5                   10                  15

Ser Ala Gln Leu Pro Ser Pro Thr Asn Gly Lys Lys Trp Glu Lys Val
            20                  25                  30

Glu Gln Leu Ser Asp Glu Phe Asn Gly Asn Ser Ile Asp Thr Asn Lys
        35                  40                  45

Trp Tyr Asp Tyr His Pro Phe Trp Gly Arg Ala Pro Ser Asn Phe
    50                  55                  60

Lys Lys Gly Asn Ala Phe Val Ser Asp Gly Phe Leu Asn Leu Arg Ser
65                  70                  75                  80

Thr Leu Arg Lys Glu Pro Ser Ser Val Gln Asp Pro Phe Lys Asp Ile
                85                  90                  95

Trp Val Asp Ala Ala Ala Val Ser Lys Thr Lys Ala Gln Pro Gly
                100                 105                 110

Tyr Tyr Tyr Glu Ala Arg Phe Lys Ala Ser Ser Leu Ser Met Thr Ser
            115                 120                 125

Ser Phe Trp Phe Arg Val Gly Gln Phe Ser Glu Ile Asp Val Ile Glu
    130                 135                 140

His Ile Gly Asn Pro Ser Lys Glu Asn Arg Gln Asp Asp Leu Pro Tyr
145                 150                 155                 160

Gln Tyr His Val Asn Thr His Tyr Tyr Gly Lys His Ala Gly Leu Gln
                165                 170                 175

Pro Leu Gly Thr Glu Tyr Lys Met Pro Gly Arg Gly Arg Asp Asn Phe
            180                 185                 190

Tyr Thr Tyr Gly Phe Trp Trp Lys Ser Pro Asn Glu Leu Leu Phe Tyr
    195                 200                 205

Phe Asn Gly Lys Gln Val Met Arg Ile Val Pro Arg Val Pro Leu Asp
210                 215                 220

Glu Leu Arg Met Ile Phe Asp Thr Glu Val Phe Pro Phe Ala Thr
225                 230                 235                 240

Ala Gly Val Ala Asn Ile Gly Leu Pro Lys Pro Glu Asn Leu Arg Asp
                245                 250                 255

Asn Ser Lys Asn Thr Met Lys Val Asp Trp Val Arg Val Tyr Lys Leu
            260                 265                 270

Val Asp Gly Thr Ala Ala Glu Asp Ser Ser Asp Ala Pro Ile Gly Ser
    275                 280                 285

Tyr Ile Ser Leu Lys Lys Thr Gln Gly Asp Gly Lys Phe Val Thr Gly
290                 295                 300

Glu Lys Asp Gly Ser Gln Leu Val Ala Arg Gly Ser Thr Val Gln Ser
305                 310                 315                 320

Trp Glu Lys Phe Lys Val Glu Lys His Pro Lys Gly Gly Ile Thr Leu
                325                 330                 335

Lys Ala Asn Ser Asn Gly Lys Tyr Val Gln Val Gln Gly Ser Asp Ile
            340                 345                 350

Asn Lys Pro Val Arg Ala Ala Gly Asp Phe Gln Gly Asp Trp Glu Gln
        355                 360                 365

Phe Glu Trp Lys Ser Lys Gly Asn Gly Leu Val Ala Leu Lys Asn Val
    370                 375                 380

Leu Thr Gly Lys Trp Leu Gln Ala Pro Trp Thr Glu Asn Asn Ala Ile
385                 390                 395                 400

Ile Arg Pro Lys Gly Pro Val Asp Asn Gly Trp Glu Thr Phe Ala Trp
                405                 410                 415
```

```
Lys Lys Glu Thr Ser Pro Thr Ala Ser Thr Ala Leu Ser Ala Gln Leu
            420                 425                 430

Glu Thr Lys Thr Val Asp Gly Ile Arg Val Tyr Pro Ser Pro Ala Ser
            435                 440                 445

Glu Thr Leu Thr Ile Glu Gly Val Gly Glu Asn Gly Leu Arg Val
            450                 455                 460

Phe Asp Ser Thr Gly Asn Pro Val Leu Lys Lys Glu Gly Ile Leu Gly
465                 470                 475                 480

Arg Lys Glu Arg Leu Asn Val Ser Gly Leu Ile Lys Gly Asn Tyr Leu
                485                 490                 495

Leu Arg Thr Gly Ser Gly Glu Gln Thr Trp Phe Gln Lys Asn
                500                 505                 510

<210> SEQ ID NO 3
<211> LENGTH: 264
<212> TYPE: PRT
<213> ORGANISM: Artificial
<220> FEATURE:
<223> OTHER INFORMATION: Recombinant porphyranase A
<220> FEATURE:
<221> NAME/KEY: MISC_FEATURE
<222> LOCATION: (1)..(8)
<223> OTHER INFORMATION: Introduced by the vector
<220> FEATURE:
<221> NAME/KEY: MISC_FEATURE
<222> LOCATION: (9)..(64)
<223> OTHER INFORMATION: Porphyranase

<400> SEQUENCE: 3

His His His His His Gly Ser Gln Leu Pro Ser Pro Thr Asn Gly
1               5                   10                  15

Lys Lys Trp Glu Lys Val Glu Gln Leu Ser Asp Glu Phe Asn Gly Asn
            20                  25                  30

Ser Ile Asp Thr Asn Lys Trp Tyr Asp Tyr His Pro Phe Trp Glu Gly
            35                  40                  45

Arg Ala Pro Ser Asn Phe Lys Lys Gly Asn Ala Phe Val Ser Asp Gly
        50                  55                  60

Phe Leu Asn Leu Arg Ser Thr Leu Arg Lys Glu Pro Ser Ser Val Gln
65                  70                  75                  80

Asp Pro Phe Lys Asp Ile Trp Val Asp Ala Ala Ala Val Ser Lys
                85                  90                  95

Thr Lys Ala Gln Pro Gly Tyr Tyr Tyr Glu Ala Arg Phe Lys Ala Ser
            100                 105                 110

Ser Leu Ser Met Thr Ser Ser Phe Trp Phe Arg Val Gly Gln Phe Ser
            115                 120                 125

Glu Ile Asp Val Ile Glu His Ile Gly Asn Pro Ser Lys Glu Asn Arg
130                 135                 140

Gln Asp Asp Leu Pro Tyr Gln Tyr His Val Asn Thr His Tyr Gly
145                 150                 155                 160

Lys His Ala Gly Leu Gln Pro Leu Gly Thr Glu Tyr Lys Met Pro Gly
                165                 170                 175

Arg Gly Arg Asp Asn Phe Tyr Thr Tyr Gly Phe Trp Lys Ser Pro
            180                 185                 190

Asn Glu Leu Leu Phe Tyr Phe Asn Gly Lys Gln Val Met Arg Ile Val
            195                 200                 205

Pro Arg Val Pro Leu Asp Glu Glu Leu Arg Met Ile Phe Asp Thr Glu
210                 215                 220
```

Val Phe Pro Phe Ala Thr Ala Gly Val Ala Asn Ile Gly Leu Pro Lys
225                 230                 235                 240

Pro Glu Asn Leu Arg Asp Asn Ser Lys Asn Thr Met Lys Val Asp Trp
            245                 250                 255

Val Arg Val Tyr Lys Leu Val Asp
            260

<210> SEQ ID NO 4
<211> LENGTH: 882
<212> TYPE: DNA
<213> ORGANISM: Zobellia galactanivorans
<220> FEATURE:
<221> NAME/KEY: sig_peptide
<222> LOCATION: (1)..(63)

<400> SEQUENCE: 4

```
atgaagcttt ccaaccaatt cctaataaca attaccctac taatcacaag tattacattc      60
gctcaagaag ctccacattt taagcctgga gaagacccaa ggcaacctca tcaggaatgg     120
aaattaattg aaaacatgtc cgatgaattt gaagggaaaa agatagatga aaaaaatgg     180
cagatttcgg gccaaggatg gataggtcgc gctccgggat tgtttcttgc agaaaatatt    240
tccttaaata acggaagttt acaaataact acaactatgc tgccagaacc tatagtcaaa    300
aacaataaaa cctatacgca cggaggtggt tacgttggct caagaaatgg tatgacctat    360
ggctattatg agtgcgaaat gaaagccaac aaaaccttca tgtcctctac attttggtta    420
attaatgaag ggaaagaccg attaggatgc gacaaaagaa caacggaatt ggacattcag    480
gaatctgttg acaaataac gatgatgcc gactggatga atactttga ccaaaccatg       540
aactccaata cccacagtag aaatattccg gagggatgtg aatacgaaaa aggatcgagc    600
aaaggcaaag cggagttagg aggaaaagca tacgaagatt ccatgtttta tggtgtttgg    660
tggaaatcta aggatgaaat tatattttc ttggacggca agatgcaatc taaagtaacg    720
ccccggccg atttgatat tgaaatgtat ttacgaatgg tcgttgagac ctatgattgg     780
aatccggtac ctaaagacgg cggcatgaca ggttcaaaag aagatagaac tacaacgtac    840
aattgggtaa ggtcatggca attggttgat tcaaagaatt aa                      882
```

<210> SEQ ID NO 5
<211> LENGTH: 293
<212> TYPE: PRT
<213> ORGANISM: Zobellia galactanivorans
<220> FEATURE:
<221> NAME/KEY: SIGNAL
<222> LOCATION: (1)..(21)

<400> SEQUENCE: 5

Met Lys Leu Ser Asn Gln Phe Leu Ile Thr Ile Thr Leu Leu Ile Thr
1               5                   10                  15

Ser Ile Thr Phe Ala Gln Glu Ala Pro His Phe Lys Pro Gly Glu Asp
            20                  25                  30

Pro Arg Gln Pro His Gln Glu Trp Lys Leu Ile Glu Asn Met Ser Asp
        35                  40                  45

Glu Phe Glu Gly Lys Lys Ile Asp Glu Lys Lys Trp Gln Ile Ser Gly
    50                  55                  60

Gln Gly Trp Ile Gly Arg Ala Pro Gly Leu Phe Leu Ala Glu Asn Ile
65                  70                  75                  80

Ser Leu Asn Asn Gly Ser Leu Gln Ile Thr Thr Thr Met Leu Pro Glu
                85                  90                  95

```
Pro Ile Val Lys Asn Asn Lys Thr Tyr Thr His Gly Gly Tyr Val
            100                 105                 110

Gly Ser Arg Asn Gly Met Thr Tyr Gly Tyr Tyr Glu Cys Glu Met Lys
        115                 120                 125

Ala Asn Lys Thr Phe Met Ser Ser Thr Phe Trp Leu Ile Asn Glu Gly
    130                 135                 140

Lys Asp Arg Leu Gly Cys Asp Lys Arg Thr Thr Glu Leu Asp Ile Gln
145                 150                 155                 160

Glu Ser Val Gly Gln Ile Thr Asn Asp Ala Asp Trp Met Lys Tyr Phe
                165                 170                 175

Asp Gln Thr Met Asn Ser Asn Thr His Ser Arg Asn Ile Pro Glu Gly
            180                 185                 190

Cys Glu Tyr Glu Lys Gly Ser Ser Lys Gly Lys Ala Glu Leu Gly Gly
        195                 200                 205

Lys Ala Tyr Glu Asp Phe His Val Tyr Gly Val Trp Trp Lys Ser Lys
210                 215                 220

Asp Glu Ile Ile Phe Phe Leu Asp Gly Lys Met Gln Ser Lys Val Thr
225                 230                 235                 240

Pro Pro Ala Asp Phe Asp Ile Glu Met Tyr Leu Arg Met Val Val Glu
                245                 250                 255

Thr Tyr Asp Trp Asn Pro Val Pro Lys Asp Gly Met Thr Gly Ser
            260                 265                 270

Lys Glu Asp Arg Thr Thr Thr Tyr Asn Trp Val Arg Ser Trp Gln Leu
        275                 280                 285

Val Asp Ser Lys Asn
    290

<210> SEQ ID NO 6
<211> LENGTH: 280
<212> TYPE: PRT
<213> ORGANISM: Artificial
<220> FEATURE:
<223> OTHER INFORMATION: Recombinant porphyranase B
<220> FEATURE:
<221> NAME/KEY: MISC_FEATURE
<222> LOCATION: (1)..(8)
<223> OTHER INFORMATION: Introduced by the vector
<220> FEATURE:
<221> NAME/KEY: MISC_FEATURE
<222> LOCATION: (9)..(280)
<223> OTHER INFORMATION: Porphyranase

<400> SEQUENCE: 6

His His His His His Gly Ser Gln Glu Ala Pro His Phe Lys Pro
1               5                   10                  15

Gly Glu Asp Pro Arg Gln Pro His Gln Glu Trp Lys Leu Ile Glu Asn
                20                  25                  30

Met Ser Asp Glu Phe Glu Gly Lys Lys Ile Asp Glu Lys Lys Trp Gln
            35                  40                  45

Ile Ser Gly Gln Gly Trp Ile Gly Arg Ala Pro Gly Leu Phe Leu Ala
50                  55                  60

Glu Asn Ile Ser Leu Asn Asn Gly Ser Leu Gln Ile Thr Thr Thr Met
65                  70                  75                  80

Leu Pro Glu Pro Ile Val Lys Asn Asn Lys Thr Tyr Thr His Gly Gly
                85                  90                  95

Gly Tyr Val Gly Ser Arg Asn Gly Met Thr Tyr Gly Tyr Tyr Glu Cys
            100                 105                 110
```

-continued

```
Glu Met Lys Ala Asn Lys Thr Phe Met Ser Ser Thr Phe Trp Leu Ile
        115                 120                 125
Asn Glu Gly Lys Asp Arg Leu Gly Cys Asp Lys Arg Thr Thr Glu Leu
    130                 135                 140
Asp Ile Gln Glu Ser Val Gly Gln Ile Thr Asn Asp Ala Asp Trp Met
145                 150                 155                 160
Lys Tyr Phe Asp Gln Thr Met Asn Ser Asn Thr His Ser Arg Asn Ile
                165                 170                 175
Pro Glu Gly Cys Glu Tyr Glu Lys Gly Ser Ser Lys Gly Lys Ala Glu
            180                 185                 190
Leu Gly Gly Lys Ala Tyr Glu Asp Phe His Val Tyr Gly Val Trp Trp
        195                 200                 205
Lys Ser Lys Asp Glu Ile Ile Phe Phe Leu Asp Gly Lys Met Gln Ser
    210                 215                 220
Lys Val Thr Pro Pro Ala Asp Phe Asp Ile Glu Met Tyr Leu Arg Met
225                 230                 235                 240
Val Val Glu Thr Tyr Asp Trp Asn Pro Val Pro Lys Asp Gly Gly Met
                245                 250                 255
Thr Gly Ser Lys Glu Asp Arg Thr Thr Thr Tyr Asn Trp Val Arg Ser
            260                 265                 270
Trp Gln Leu Val Asp Ser Lys Asn
        275                 280

<210> SEQ ID NO 7
<211> LENGTH: 36
<212> TYPE: DNA
<213> ORGANISM: Artificial
<220> FEATURE:
<223> OTHER INFORMATION: primer

<400> SEQUENCE: 7
ggggggggat cccaattacc atctcctaca aacggg                              36

<210> SEQ ID NO 8
<211> LENGTH: 37
<212> TYPE: DNA
<213> ORGANISM: Artificial
<220> FEATURE:
<223> OTHER INFORMATION: primer

<400> SEQUENCE: 8
ggggggggat cccaagaagc tccacatttt aagcctg                             37

<210> SEQ ID NO 9
<211> LENGTH: 40
<212> TYPE: DNA
<213> ORGANISM: Artificial
<220> FEATURE:
<223> OTHER INFORMATION: primer

<400> SEQUENCE: 9 cccccccgaat tcttagtcaa ccaatttata cacccgtacc                         40

<210> SEQ ID NO 10
<211> LENGTH: 41
<212> TYPE: DNA
<213> ORGANISM: Artificial
<220> FEATURE:
<223> OTHER INFORMATION: primer
```

```
<400> SEQUENCE: 10 cccccgaat tcttaattct ttgaatcaac caattgccat g                        41
```